(12) United States Patent
Lunsford

(10) Patent No.: US 8,095,653 B2
(45) Date of Patent: Jan. 10, 2012

(54) SYSTEM AND METHOD FOR MONITORING AND DISPLAYING RADIOLOGY IMAGE TRAFFIC

(75) Inventor: Michael Lunsford, Centennial, CO (US)

(73) Assignee: L-Cubed Medical Informatics, LLC, Centennial, CO (US)

( * ) Notice: Subject to any disclaimer, the term of this patent is extended or adjusted under 35 U.S.C. 154(b) by 0 days.

(21) Appl. No.: 13/152,104

(22) Filed: Jun. 2, 2011

(65) Prior Publication Data

US 2011/0238827 A1 Sep. 29, 2011

Related U.S. Application Data

(62) Division of application No. 11/367,089, filed on Mar. 2, 2006, now Pat. No. 7,979,522.

(60) Provisional application No. 60/685,446, filed on May 27, 2005.

(51) Int. Cl.
G06F 15/173 (2006.01)

(52) U.S. Cl. .................. 709/224; 709/223; 709/225

(58) Field of Classification Search ........... 709/223–225
See application file for complete search history.

(56) References Cited

U.S. PATENT DOCUMENTS

| | | | |
|---|---|---|---|
| 5,949,757 A * | 9/1999 | Katoh et al. ............... 370/232 |
| 6,424,624 B1 * | 7/2002 | Galand et al. ............. 370/231 |
| 7,219,300 B2 | 5/2007 | Arquie et al. |
| 7,546,368 B2 * | 6/2009 | Drees et al. ............... 709/224 |
| 7,979,522 B2 | 7/2011 | Lunsford |
| 2001/0021176 A1 * | 9/2001 | Mimura et al. ............ 370/235 |
| 2001/0051881 A1 * | 12/2001 | Filler ............................. 705/3 |
| 2002/0129140 A1 * | 9/2002 | Peled et al. ................. 709/224 |
| 2003/0169764 A1 * | 9/2003 | Lavigne et al. ............ 370/463 |
| 2004/0143594 A1 * | 7/2004 | Kalies ...................... 707/103 R |
| 2004/0181433 A1 * | 9/2004 | Blair ............................ 705/2 |
| 2005/0203771 A1 * | 9/2005 | Achan ........................... 705/2 |
| 2005/0234915 A1 * | 10/2005 | Ricciulli ..................... 707/10 |
| 2005/0236474 A1 * | 10/2005 | Onuma et al. ............. 235/382 |
| 2006/0036707 A1 * | 2/2006 | Singh et al. ................ 709/217 |
| 2006/0123101 A1 * | 6/2006 | Buccella et al. ........... 709/223 |
| 2007/0043535 A1 | 2/2007 | Belden |
| 2007/0214412 A1 * | 9/2007 | Arquie et al. .............. 715/526 |
| 2008/0091473 A1 * | 4/2008 | Choppin ........................ 705/3 |
| 2008/0287118 A1 * | 11/2008 | Seppanen .................. 455/423 |
| 2009/0080408 A1 * | 3/2009 | Natoli et al. ............... 370/351 |

OTHER PUBLICATIONS

U.S. Appl. No. 11/367,089, filed Mar. 2, 2006, Office Action mailed Jul. 20, 2009, 10 pgs.
U.S. Appl. No. 11/367,089, filed Mar. 2, 2006, Amendment and Response filed Nov. 20, 2009, 7 pgs.
U.S. Appl. No. 11/367,089, filed Mar. 2, 2006, Notice Re: Non-Compliant Amendment mailed Dec. 18, 2009, 2 pgs.

(Continued)

*Primary Examiner* — Mohamed Wasel
(74) *Attorney, Agent, or Firm* — Merchant & Gould P.C.

(57) ABSTRACT

An embodiment of the present invention includes a system and method for detecting and monitoring confidential and DICOM image traffic on a computing device in a PACS network. Embodiments of the present invention protect patient confidentiality by preventing the simultaneous display of confidential images and patient identification information when measuring and displaying the image data. The system detects and measures the transfer of confidential images and stores and displays information included in only the non-confidential headers of the images. The system monitors and warns (such as via email and/or pagers) PACS administrators of system slowdowns as a result of the data gathered.

6 Claims, 14 Drawing Sheets

OTHER PUBLICATIONS

U.S. Appl. No. 11/367,089, filed Mar. 2, 2006, Amendment and Response filed Dec. 28, 2009, 10 pgs.

U.S. Appl. No. 11/367,089, filed Mar. 2, 2006, Final Office Action mailed Apr. 9, 2010, 10 pgs.

U.S. Appl. No. 11/367,089, filed Mar. 2, 2006, Amendment and Response filed Jun. 8, 2010, 8 pgs.

U.S. Appl. No. 11/367,089, filed Mar. 2, 2006, Notice of Allowance mailed Mar. 2, 2011, 12 pgs.

* cited by examiner

SYSTEM AND METHOD FOR MONITORING AND DISPLAYING RADIOLOGY IMAGE TRAFFIC

RELATED APPLICATIONS

This application claims priority to co-pending application No. PCT/US06/20485, filed May 24, 2006, which application claims priority to U.S. application Ser. No. 11/367,089, filed Mar. 2, 2006. In addition, this application is a divisional application of and claims priority to U.S. application Ser. No. 11/367,089, filed Mar. 2, 2006, which application claims priority of U.S. Provisional Application Ser. No. 60/685,446, filed May 27, 2005, which application is hereby incorporated herein by reference.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND OF THE INVENTION

Electronic data is fast replacing old-fashioned paper, film and hard copy records in the medical industry. One type of data that is very common in the medical field is image data, referred to in the industry generally as Digital Imaging and Communication in Medicine, or "DICOM," data. Most modern medical imaging devices (referred to hereafter generally as a 'modality' or 'modalities') are now designed to generate DICOM data and send it to a medical database referred to as Picture Archiving and Communication System, or "PACS system" for short.

Modalities include such devices known as Computed Tomography (CT or "Cat") Scanners, Magnetic Resonance Imagers (MRIs), Positron Emission Tomography (PET) devices, Nuclear Medicine (NM) devices, Ultra-Sound (US) scanners, and Computed Radiography (CR) scanners to name just a few. Modalities generate DICOM data, often with modality-specific data or transmission formats, which are transmitted to and archived on the PACS system through which medical practitioners can access the DICOM image data.

A PACS system stores medical images received from the modalities on computers called DICOM Servers. The DICOM servers provide central storage and access to the images. They are referred to as servers because they 'serve' up the images to radiologists and other healthcare staff for diagnostic interpretation and ongoing clinical patient care in Clinic, hospital and home settings.

A PACS network often involves hundreds of modalities that generate DICOM data, DICOM servers that store the DICOM data, and workstations that retrieve DICOM data from the archive so that it can be reviewed by medical personnel. Often each device in the PACS network uses proprietary software and hardware and generates and transmits DICOM formatted data in a device-specific format.

One common problem in PACS network administration relates to a slowdown in the transfer of images and image data on the network. Often slowdowns are not detected until a complaint is received by PACS administrator, after the slowdown has adversely impacted some user of the PACS network. The PACS administrator then must check each link in the distributed network to identify the source of the slowdown. Then the cause of the slowdown must be determined and corrected.

Slowdowns can be caused by any number of reasons including hardware failure and incompatible software on any one the devices in the PACS network. One common cause is installing a new version of software on a device, such as a modality in the network. Often it is assumed that a newer version of software will automatically work on a device because the older version works. However, because there is no universal standard, devices on the PACS network typically must be integrated into the PACS system for the device to interface properly with the rest of the PACS network. Integration is time consuming and expensive, requiring skilled technicians including the hospital's PACS administrator, the PACS system technician, and the modalities Field Service personnel. When installing a new version of software, it is often forgotten that substantial changes may have been made to the original version of the software during integration. The resulting incompatibility may cause a perceived slowdown anywhere within the entire PACS network even though the slowdown may not be discernable at the device that is the cause of the slowdown.

For example, integration of computing devices on a PACS network often involves programming the computing device to create a header of a format that the PACS network can recognize quickly and process efficiently. Often, updating software versions on computing devices will unwittingly change the Network Interface Card (NIC) settings because the PACS system-specific changes made during integration are lost or overwritten. When a DICOM image is sent to a PACS server through a NIC that has sub-optimal speed or duplex settings then it directly impacts the performance of the network.

For example, the network interface card settings of a personal computer or workstation may be unwittingly changed when installing new software from the original settings selected by the PACS administrator. Depending on the architecture of the PACS network and the computing device's location within the flow of DICOM image data, this change result in a "bottleneck" that slows data transfer throughout the PACS network. Because the change was unknown, it may take the PACS administrator a significant amount of time to identify the network interface settings as the source of the problem. This slows down the delivery of the images to healthcare providers and impacts patient care especially in critical care situations like and Emergency or Operating room environments.

In addition, these settings are often negotiated periodically such as every five minutes and can change in response to changing in the network, such as changes in the signal strength of a wireless communication.

Another problem is the false perception of a slowdown. Often, PACS network users base their perception of the network's performance on the speed at which an image is displayed on a screen after a request or the time it takes to transmit an image to the DICOM server. However, different images may differ greatly in the size of the image file, even when they are the same type of image from the same modality. Thus, users may perceive a slowdown when, in fact, the system is operating at the same speed but the user is dealing with an unexpectedly large image file. User complaints based on such false perceptions are difficult to track down by PACS administrators as they are now tasked with verifying that the system is operating appropriately.

Yet another problem is associated with handling medical data. Due to various federal and state laws regarding the confidentiality of medical data, it is important that confidential information be maintained in confidentiality by the PACS administrators and technicians tasked with maintaining the PACS network. This adds an extra layer of complexity in the administration of the PACS network because some of the medical image data on the network, particularly the patient identification information allowing DICOM images to be associated with a patient, should not be accessible by anyone looking over the shoulder of the PACS administrators.

SUMMARY OF THE INVENTION

Against this backdrop the present invention has been developed. An embodiment of the present invention includes a system and method for detecting and monitoring confidential image traffic on a computing device in a PACS network. Embodiments of the present invention protect patient confidentiality by preventing the simultaneous display of confidential images and patient identification information when measuring the image data. The system detects and measures the transfer of confidential images and stores and displays information included in only the non-confidential headers of the images.

An embodiment of the present invention may be considered a method for monitoring performance of a medical data network without violating patient confidentiality. The method includes receiving a stream of data at a network interface (NIC) of a computing device, in which the stream of data includes image data comprising data for one or more confidential images. The data for a confidential image includes a non-confidential header portion, a patient identifier portion, and an image body portion. The method calls for monitoring the stream of data at the network interface for non-confidential header portions of image data and generating, immediately after detection of a non-confidential header portion, displays to the users a graphical user interface (GUI) on a display of the computing device. The GUI displays a current flowrate of images through the network interface as a number of images received within a first period of time, such as a second.

Another embodiment of the present invention includes a system for monitoring performance of a medical data network without violating patient confidentiality. The system includes at least one first image traffic monitoring system operating on one of a plurality of first computing devices. The first image traffic monitoring system is capable of detecting the transfer of confidential images between the first computing device and the medical data network and storing non-confidential image traffic measurement data, including non-confidential data copied from the confidential images and data describing the number of confidential images transferred over time. The system also includes a network traffic analysis system operating on a second computing device. The network traffic analysis system is capable of receiving and analyzing image traffic data from the first image traffic monitoring system and generating warnings to an administrator of the medical data network if the image traffic data indicates that the transfer of confidential images between the first computing device and the medical data network falls below a threshold set by the administrator.

Another embodiment of the present invention includes a graphical user interface comprising a first virtual gauge displaying the average number of images per first period of time received at a network interface over a second period of time (e.g., the number images per second received at the network interface averaged over 5 five seconds) and a live graph element displaying a graph of a number of images received at the network interface per first period of time for a third period of time.

These and various other features as well as advantages which characterize the present invention will be apparent from a reading of the following detailed description and a review of the associated drawings.

DETAILED DESCRIPTION

An embodiment of the present invention includes a system and method for detecting and monitoring confidential and DICOM image traffic on a computing device in a PACS network. Embodiments of the present invention protect patient confidentiality by preventing the simultaneous display of confidential images and patient identification information when measuring and displaying the image data. The system detects and measures the transfer of confidential images and stores and displays information included in only the non-confidential headers of the images. The system monitors and warns (such as via email and/or pagers) PACS administrators of system slowdowns as a result of the data gathered.

For the purposes of this specification, DICOM images are electronic images generated by a modality for viewing or storage. DICOM images include images that conform to the current DICOM Standard published by the National Electrical Manufacturers Association, copyright 2004 which is hereby incorporated herein by reference, conform to future DICOM standards or conform to some other recognized standard for digital medical images, for example based on a self-defining language such as .XML. In addition, not all DICOM images strictly comply with the DICOM standard and, as will be described in greater detail below, DICOM images include images generated by modalities that are recognizable based on features contained within the image data.

The DICOM Standard includes a standard format for image files so that metadata associated with the image, referred to as "file meta information" can be transferred with the image or images as a single logical unit. The file meta information includes identifying information on the encapsulated image data set. All DICOM images begin with a header conforming the DICOM Standard. This header consists of a 128 byte file preamble, followed by a 4 byte 'DICM' prefix, followed by the file meta elements shown in Table 7.1-1 of P3.10-2004 of the DICOM Standard. The four byte DICOM prefix under the standard must contain the character string "DICM" encoded as uppercase characters of the ISO 8859 GO Character Repertoire. The DICOM Standard requires that this header shall be present in every DICOM file. In an embodiment, the 128 byte file preamble may be all set to OOH in the ISO 8859 GO Character Repertoire or otherwise to "0" or null. In another embodiment, the preamble may be some user selected byte series.

In addition, many modalities now include information in headers that is not part of the DICOM Standard. In particular, some modalities include in an image header one of the following statements preceded by a null: ORIGINAL\PRIMARY; DERIVED\SECONDARY; DERIVED\PRIMARY; or ORIGINAL\SECONDARY. Often, modalities using the above-listed statements omit the DICM encoding in the header and so do not strictly conform to the DICOM Standard.

Figure 1:
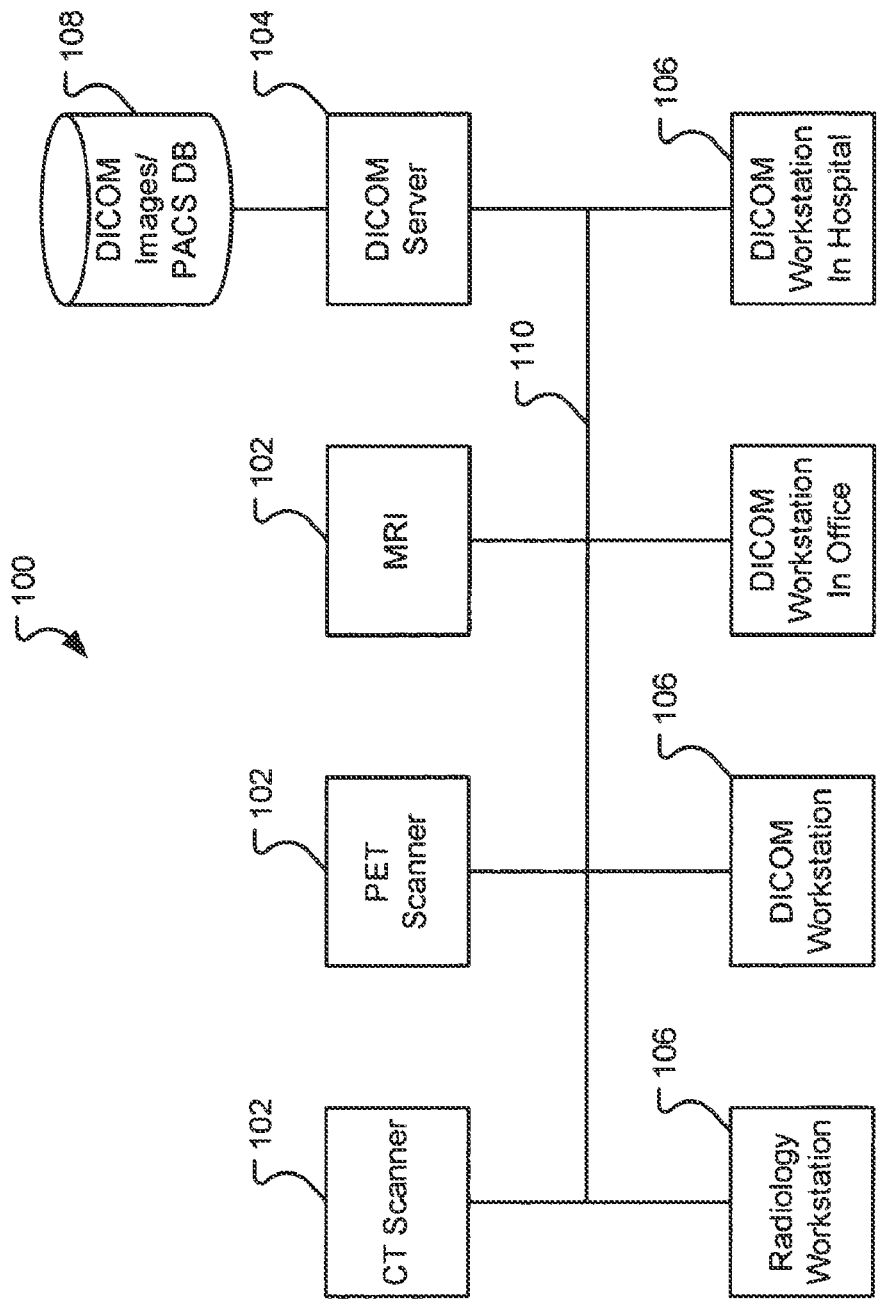
FIG. 1 is an illustration of an exemplified Picture Archiving and Communication System (PACS) network.

FIG. 1 is an illustration of an exemplified Picture Archiving and Communication System (PACS) network. The PACS network 100 potentially includes many different types of computing devices. Such devices include modalities 102 that are capable of creating DICOM images; PACS servers 104 for storing and retrieving DICOM images interfacing with one or more PACS databases 108 containing archived DICOM images; and workstations 106 for viewing DICOM images. Other computing devices (not shown) that handle or manipulate DICOM data in some way are also possible to measure with this product.

The computing devices 102, 104, 106 are connected via a network 110. The network could be the Internet, but given the confidentiality issues, it is general practice and it is anticipated that most PACS systems 100 will use some form of a private local area network (LAN) or wide area network (WAN) or the like for some if not all of the DICOM image traffic. In alternate embodiments, different components of the system may be communicatively coupled differently, for example each may be coupled directly to each other wirelessly or by a local or wide area network (WAN), use SSL encryption or delivered via VPN or the like.

Modalities 102 generate DICOM images and transmit them to PACS servers 104 for archiving and storage, which can then be retrieved by the viewing workstations 106. The modalities 102 may also directly transmit DICOM images to viewing workstations 106 using local PACS software, such as for example eFilm Workstation™.

Embodiments of the present invention are DICOM image traffic monitoring system suitable for implementation on various computing devices 102, 104, and 106 for monitoring DICOM image traffic into and or out of the computing device. A DICOM image traffic monitoring system identifies DICOM images transmitted between the network and the computing device and provides statistical and report information in substantially real time through a display to the user of the computing device and, potentially, to a central image traffic management system.

Figure 2:
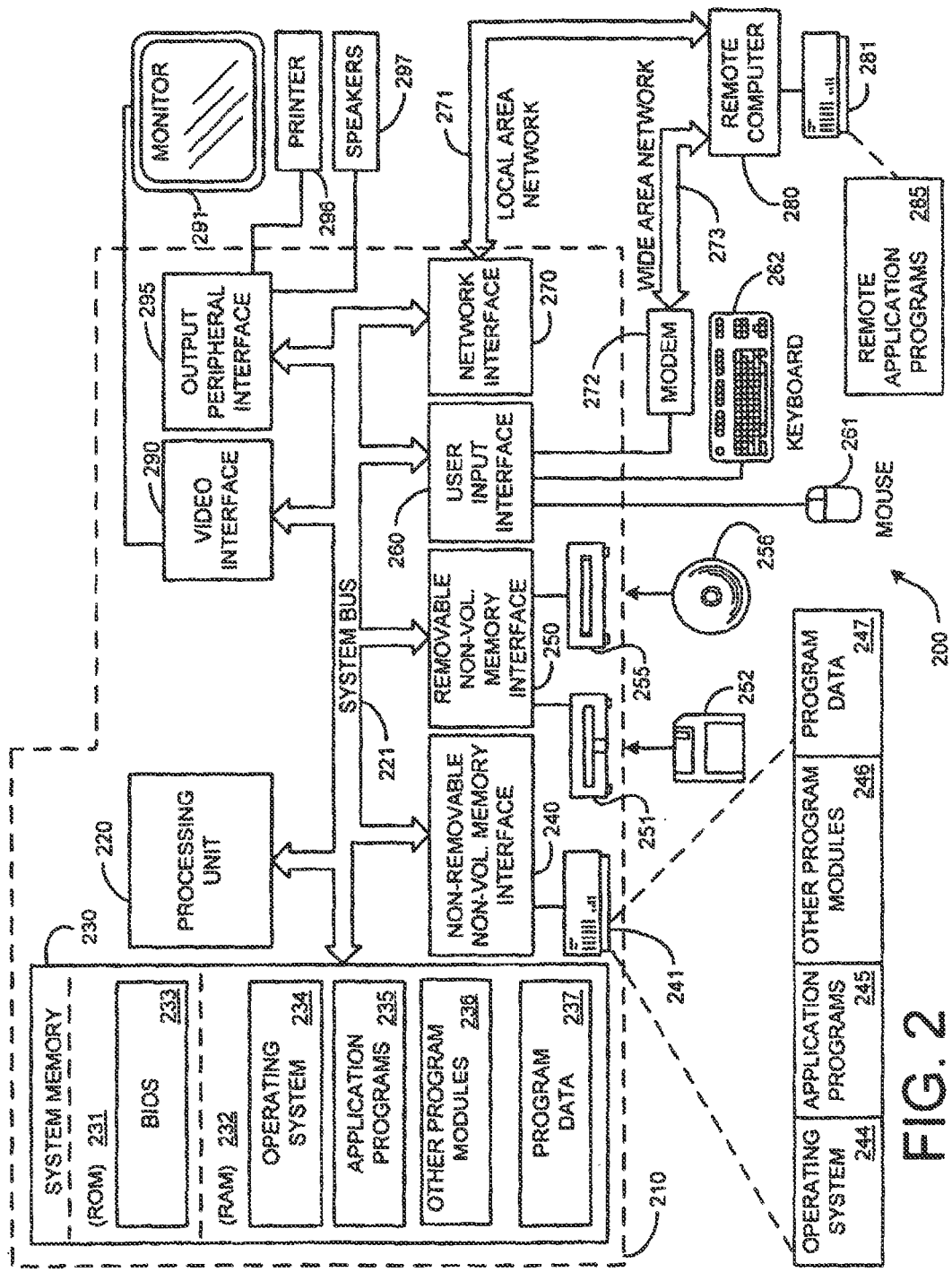
FIG. 2 is an illustration of an exemplified computing device environment on which an embodiment of an image traffic monitoring system may be implemented.

FIG. 2 is an illustration of an exemplified computing device environment on which an embodiment of an image traffic monitoring system may be implemented. The computing system environment 200 is only one example of a suitable computing environment and is not intended to suggest any limitation as to the scope of use or functionality of the invention. Neither should the computing environment 200 be interpreted as having any dependency or requirement relating to anyone or combination of components illustrated in the exemplary operating environment 200.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 2, an exemplary computer system 200 for implementing the invention includes a general purpose-computing device in the form of a computing device 210. Components of the computing device 210 may include, but are not limited to, a processing unit 220, a system memory 230, and a system bus 221 that couples various system components including the system memory 230 to the processing unit 220. The system bus 221 may be any of several types of bus structures including a memory bus or memory controller, a peripheral bus, or a local bus using any of a variety of bus architectures. By way of example, and not limitation, such architectures include the Industry Standard Architecture (ISA) bus, the Micro Channel Architecture (MCA) bus, the Enhanced ISA (EISA) bus, the Video Electronics Standards Association (VESA) local bus, and the Peripheral Component Interconnect (PCI) bus, also known as the Mezzanine bus.

Computing device 210 typically includes a variety of computer readable media. Computer readable media can be any available media that can be accessed by the computing device 210 and includes both volatile and nonvolatile media and removable and non-removable media. By way of example, and not limitation, computer readable media may comprise computer storage media and communication media. Computer storage media includes volatile, nonvolatile, removable, and non-removable media implemented in any method or technology for storage of information such as computer readable instructions, data structures, program modules, or other data. Computer storage media includes, but is not limited to, RAM, ROM, EEPROM, flash memory or other memory technology, COROM, digital versatile disks (OVO) or other optical disk storage, magnetic cassettes, magnetic tape, magnetic disk storage or other magnetic storage devices, or any other medium which can be used to store the desired information and which can accessed by computing device 210. Communication media typically embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media, such as a wired network or direct wired connection, and wireless media, such as acoustic, RF, infrared, and other wireless media. Combinations of the any of the above should also be included within the scope of computer readable media.

The system memory 230 includes computer storage media in the form of volatile and/or nonvolatile memory, such as read only memory (ROM) 231 and random access memory (RAM) 232. A basic input/output system 233 (BIOS), containing the basic routines that help to transfer information between elements within computing device 210, such as during start-up, is typically stored in ROM 231. RAM 232 typically contains data and/or program modules that are immediately accessible to and/or presently being operated on by processing unit 220. By way of example, and not limitation, FIG. 2 illustrates operating system 234, application programs 235, other program modules 236, and program data 237.

The computing device 210 may also include other removable/non-removable, volatile/nonvolatile computer storage media. By way of example only, FIG. 2 illustrates a computing device 210 with a non-removable, non-volatile memory interface 240 that reads from or writes to non-removable, nonvolatile magnetic media 241, such as a hard drive. Computer 210 may also include a non-volatile memory interface 250 that reads from or writes to a device 251, such as a disk drive, that reads from or writes to a removable, non-volatile media 252, such as a magnetic disk. In addition, the computing device 210 may include an optical disk drive 255 that reads from or writes to a removable, nonvolatile optical disk 256, such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 241 is typically connected to the system bus 221 through a non-removable memory interface, such as interface 240, and magnetic disk drive 251 and optical disk drive 255 are typically connected to the system bus 221 by a removable memory interface, such as interface 250.

The drives and their associated computer storage media discussed above and illustrated in FIG. 2, provide storage of computer readable instructions, data structures, program modules, and other data for the computing device 210. For example, hard disk drive 241 is illustrated as storing operating system 244, application programs 245, other program modules 246, and program data 247, which can either be the same as or different from operating system 234, application programs 235, other program modules 236, and program data 237. Operating system 244, application programs 245, other program modules 246, and program data 247 are given different numbers here to illustrate that, at a minimum, they are different copies. A user may enter commands and information into the computing device 210 through a user input interface 260 connected to user input devices, such as a keyboard 262 and pointing device 261, commonly referred to as a mouse, trackball, or touch pad. Other input devices (not shown) may include a microphone, joystick, game pad, satellite dish, scanner, or the like. These and other input devices are often connected to the processing unit 220 through a user input interface 260 that is coupled to the system bus 221, but may be connected by other interfaces and bus structures, such as a parallel port, game port, or a universal serial bus (USB).

A monitor 291 or other type of display device is also connected to the system bus 221 via an interface, such as a video interface 290. In addition to the monitor 291, the computer 210 may also include other peripheral output devices such as speakers 297 and printer 296, which may be connected through an output peripheral interface 295.

The computing device 210 may operate in a networked environment using logical connections to one or more remote computers, such as a remote computer 280. The remote computer 280 may be a personal computer, a server, a router, a network PC, a peer device, or other common network node, and typically includes many or all of the elements described above relative to the computing device 210, although only a memory storage device 281 has been illustrated in FIG. 2. The logical connections depicted in FIG. 2 include a local area network (LAN) 271 and a wide area network (WAN) 273, but may also include other networks, such as wireless networks. Such networking environments are commonplace in offices, enterprisewide computer networks, intranets, and the Internet.

When used in a LAN networking environment, the computing device 210 is connected to the LAN 271 through a network interface or adapter 270. When used in a WAN networking environment, the computing device 210 typically includes a modem 272 or other means for establishing communications over the WAN 273, such as the Internet. The modem 272, which may be internal or external, may be connected to the system bus 221 via the user input interface 260, or other appropriate mechanism. In a networked environment, program modules depicted relative to the computing device 210, or portions thereof, may be stored in the remote memory storage device 281. By way of example, and not limitation, the remote application programs 285 reside on memory device 281. It will be appreciated that the network connections shown are exemplary and other means of establishing a communications link between the computers may be used.

In an embodiment, one of the applications 245 is a DICOM image traffic monitoring system adapted to work with the operating system 244 of the computing device 210. The DICOM image traffic monitoring system monitors data traffic, alternately referred to as a data stream, received by the network interface 270. This data traffic may be incoming (i.e., received from an external computing device 280) or may be outgoing (i.e., being transmitted to an external computing device 280). It is anticipated that most computing devices 210 in a PACS system will primarily, if not completely, operate in one mode, incoming or outgoing. A PACS server or a DICOM Image Broker is an example of a computing device that is likely to operate both modes. In an embodiment, incoming data and outgoing data are monitored separately and independently.

Embodiments of the DICOM image traffic monitoring systems on a computing device identify DICOM images by monitoring data traffic at the network interface of the computing device. In an embodiment, a DICOM image traffic monitoring system on a computing device monitors a network interface for either the DICM statement preceded by a significant number of nulls or any one of the ORIGINAL\PRIMARY; DERIVED\SECONDARY; DERIVED\PRIMARY; or ORIGINAL\SECONDARY statements preceded by a null. When identifying the DICM statement, although the Standard calls for 128 nulls, for detection purposes the DICM statement preceded by less nulls (such as 64, 24, 16 or 8) can be used as an identification condition. The actual number of nulls should be chosen to ensure that the statement was not generated for some other purpose than as a header for a DICOM image, which may be dependent on the models of modalities and other computing devices in use on the PACS system. Upon determining that one of these statements was contained in data passing through the network interface, the DICOM image traffic monitoring system reports that a DICOM image has passed through the network interface.

In an embodiment, the DICOM image traffic monitoring system maintains a DICOM image receipt database in which it records information about DICOM image traffic received at the monitoring point. The image receipt database may be a database or simply a file structure containing data. In one embodiment, the DICOM image, receipt database includes a record for each DICOM image received. The record includes a timestamp of the time the image was detected, as well as a patient name from the header of each DICOM image. Other information that may included is the computing device that was sending the image and the computing device that was receiving the image. This information may be in the form of an Make and Model number of the modality or Internet Protocol (IP) address for the computing devices, or it may be some other network identifier. An image receipt record in the DICOM image receipt database may also include a source modality or image type. An image receipt record may also include an estimated size determined by recording the amount (such as in kilobytes) of data received since the last received DICOM image in the DICOM image receipt database.

In an alternative embodiment, the DICOM image receipt database may create one record for a given segment of time, such as one record per second. In the alternative embodiment, each record may include a second identifer, which may be the timestamp (e.g., a date and time to the second in a predetermined time zone), and the number of DICOM images detected during that second. The record may also include a patient's name taken from one of the DICOM image headers detected during that timestamp as well as a representative sample of some or all of the other information described above.

In addition to the image receipt database, a header database (not shown) may be maintained in which copies of some or all of the headers detected passing through the network interface are stored. These may be accessed by a PACS administrator in order to provide quick access to headers in the event of a problem.

Figure 3:
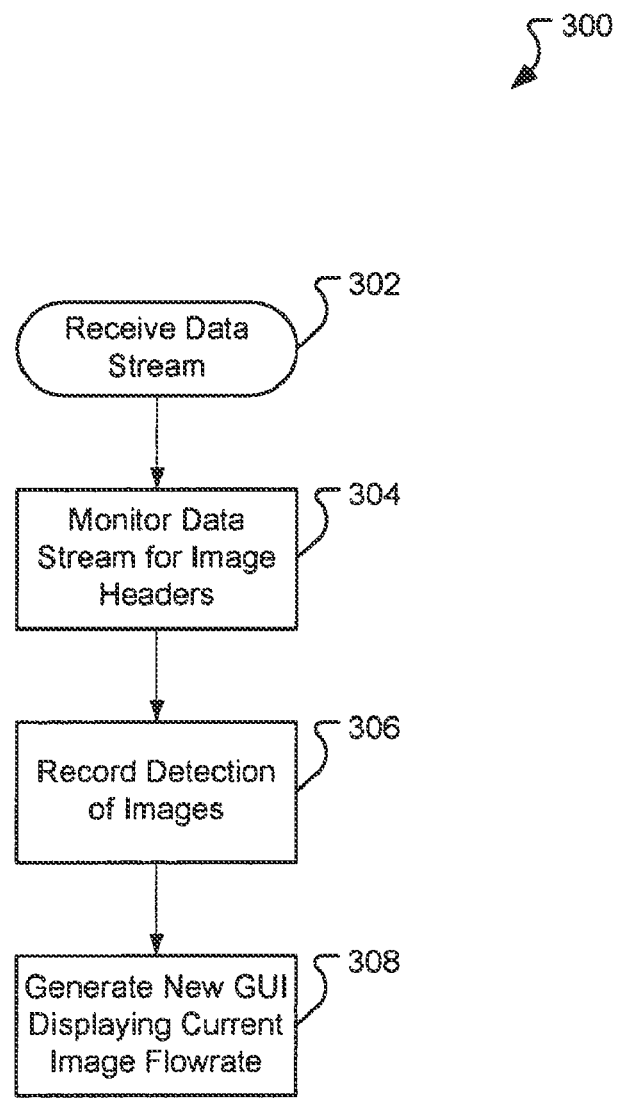
FIG. 3 illustrates an embodiment of a method for monitoring performance of a medical data network without violating patient confidentiality.

FIG. 3 illustrates an embodiment of a method for monitoring performance of a medical data network without violating patient confidentiality. In the method, a stream of data including image data is received in a receive data stream operation 302 by a network interface of a computing device that implements the DICOM image traffic monitoring system. The data stream may include DICOM image data as well as other data that occurs between computing devices on a network, such as e-mail data, and network management data and the modality or server image data itself. The data stream may be incoming, outgoing or both. For simplicity, the data flow will be described only in the context of incoming data.

The DICOM image data includes a header, as described above, including the patient's name as well as the data for the image body. In order to comply with patient confidentiality laws and regulations, unauthorized personnel must be prevented from accessing the patient's identity information and the image body. The image body may be viewed, as long as the patient remains anonymous. Likewise the patient's name may be viewed, as long as the image body associated with the patient is not disclosed.

The data received by the network interface is monitored in a monitor data traffic operation 304, such as by standard packet sniffing techniques. Packet sniffers can intercept and log traffic passing over a digital network or part of a network. As data streams back and forth over the network, the sniffer captures each packet and eventually decodes and analyzes its content according to the appropriate RFC or other specifications. A packet sniffer may look at all data in a packet or only a portion of the data in a packet. In the embodiment discussed, the packet sniffer is implemented as part of the DICOM image traffic monitoring application on the computing device and is designed to monitor data passing through the network interface. Other implementations are possible including monitoring at a software application instead of a network interface or using a stand-alone DICOM image traffic monitor that can be inserted into a network at any location.

In the monitor data traffic operation 304, the DICOM image traffic monitoring system is looking for header information that indicates that a DICOM image is passing through the monitoring point. As discussed above, in an embodiment the DICOM image traffic monitoring system monitors the network interface for either the DICM statement preceded by a significant number of nulls or any one of the ORIGINAL\PRIMARY; DERIVED\SECONDARY; DERIVED\PRIMARY; or ORIGINAL\SECONDARY statements preceded by a null.

If one of the conditions described above (i.e., data is received corresponding to the DICM statement preceded by a significant number of nulls, an ORIGINAL\PRIMARY statement preceded by a null; a DERIVED\SECONDARY statement preceded by a null; a DERIVED\PRIMARY statement preceded by a null; or an ORIGINAL\SECONDARY statement preceded by a null) is detected, the DICOM image traffic monitoring system then records the detection of a DICOM image into a DICOM image receipt database in a recording operation 306.

Recording operation 306 may include generating a timestamp of the time at which the header was detected as well as copying data out of the detected DICOM header, such as the patient's name. In addition, the amount of data (such as in kilobytes) transferred through the network interface since the last DICOM header was detected may be recorded in the receipt database. This amount of data may not be an exact measure of the size of the image, because other data traffic may be going through the network interface that is intersperced within the DICOM image data. However, because DICOM images are so large compared to most other forms of data normally on a PACS network, the amount is useful to administrators attempting to analyze the network.

In an embodiment of the present invention, if the DICOM image traffic montioring system is in operation, a graphical user interface is displayed to a user of the computing device executing the image traffic monitoring system. After detection of a newly received image header, the DICOM image traffic monitoring system generates a new graphical user interface (GUI) in a revise GUI operation 310. The new GUI replaces the previous GUI and so may be alternately referred to as generating a (new) GUI or updating or revising the GUI to reflect the current data in the image receipt database.

In an embodiment, a DICOM image traffic monitoring system GUI may include one or more interface elements in the form of virtual gauges visually displaying the current flowrate of images or kilobytes received within a specified flowrate measurement period, such as images per second or kilobytes per second. Virtual gauges are useful because the interface is immediately understood by unsophisticated users of PACS equipment and are also suited to provide information "at a glance." In addition, other virtual gauges may be provided that show, at a glance, the average flowrate of images or kilobytes during a larger period such as over the last hour, day, month, year, etc. Example GUIs are described in greater detail below.

Generation of a GUI may require some computation based on the information in the DICOM image receipt database. For example, each time a GUI is generated, the image receipt database may have to be inspected and a new average flowrate may have to be calculated for each virtual gauge interface element in a calculation operation (not shown).

In one embodiment, a new GUI is generated in response to the detection of a new image. In an alternative embodiment, a new GUI is generated periodically using a redraw period selected to ensure that relatively accurate flowrate data is always displayed. In yet another embodiment, the DICOM image traffic monitoring system may generate a new GUI using a variable period based on recent image traffic or only using periodic generation during periods of little or no traffic. For example, during long periods where no image is detected, the DICOM image traffic monitoring system may revise the GUI less often, such once every five minutes, than during periods of high traffic when it may be done in response to every detection or at some substantially high rate such as 10 or 60 times a second.

Regardless, the DICOM image traffic monitoring system is designed to redraw the GUI substantially immediately after detection of a new DICOM image. The term "substantially immediately" is used herein to indicate that the GUI may not be redrawn immediately upon detection of new image, but will be redrawn within a relatively short period in order to give the user an accurate indication of the current condition of the computing device.

As discussed above, one element of the GUI is a current flowrate element. The current flowrate element is provided to give the computing device user information concerning the current flowrate of images, such as by displaying the current flowrate in images per second or kilobytes per second in real time. However, it has been determined that displaying images per second is real time may be confusing to a user. It has been found that immediately updating the current flowrate element in a high throughput system can cause the virtual gauge of the element to change rapidly causing the "needle" on the virtual gauge to jump around, especially if the GUI is redrawn multiple times in a flowrate measurement period. In order to make the current flowrate element more useful, some smoothing of the data is required. In an embodiment, the smoothing is achieved by displaying an average flowrate based on some period slightly larger than the flowrate measure period. For example, displaying a five second average of the flowrate in images per second and revising the GUI only five or six times per second. In an alternative embodiment, other smoothing methods are used such as recording detection of images to the nearest one tenth of a second and extrapolating an average image per second flowrate based on the last two second's data.

Figure 4:
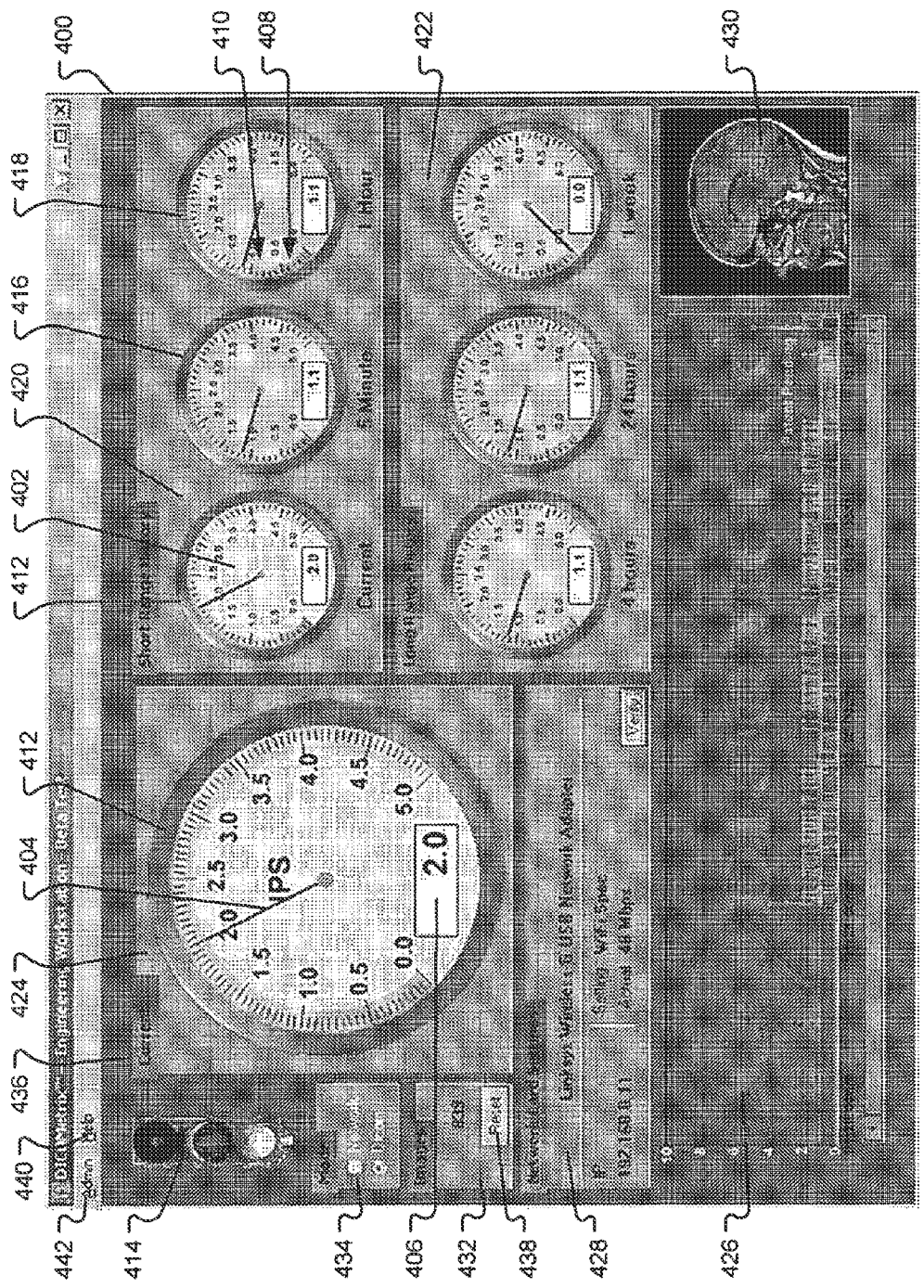
FIG. 4 is an exemplified main display GUI for use with an image traffic monitoring system displaying data in units of confidential images per second.

FIG. 4 is an exemplified main display GUI for use with an image traffic monitoring system. The main display GUI 400 shown is divided into several areas including a short range history 420, a long range history 422, and a main flowrate area 424, all using virtual gauges to display flowrate data. In addition, the GUI 400 includes a real time "live graph" element 426, a network card settings area 428, a status element 430, an image counter element 432, a display mode element 434, and a pause element 414. The GUI 400 is also provided with an Admin dropdown menu control element 440 and Help dropdown menu control element 442 to access other GUIs for the system.

In the embodiment of the GUI 400 shown, virtual gauges are used to display different flowrates of image data through the network interface. Each virtual gauge is provided with a dial face 402 with numerical markings, a needle 404 of the gauge, and a numerical display 406 of the current reading. Although difficult to see in the black and white figures, each virtual gauge is provided with a red zone 408 and yellow zone 410. The red zone 408 and yellow zone 410 are user definable for each gauge through a settings control GUI 700 described below with reference to FIG. 7. Virtual gauges are used to display average flowrates for different periods.

As discussed above, the main flowrate area 424 contains the current flowrate gauge 412 displaying a smoothed current flowrate. In the embodiment shown, the gauge displayed in the main area 424 is substantially larger than the gauges in the other areas 420, 424. The gauge displayed in the main area 424 may be user selectable. In an embodiment, a user may change the gauge contained in the main area 424 by selecting and left clicking on any gauge from the short term history 420 or the long term history 422 which transfers it to the main display area 424. A textual display area 436 in the main display area 424 indicates what virtual gauge is currently displayed in the main area 424.

In the GUI 400, the current flowrate gauge 412 is displayed in the main display area 424. The current flowrate gauge 412 illustrates the current flowrate of image data through the network interface. The flowrate of image data is presented in images per second or IPS" as shown on the face of the virtual gauge and which can also be determined from the display mode element 434 as described below. The current flowrate gauge 412 displays a smoothed current flowrate with a reading of 2.0 IPS. In an embodiment, the current flowrate gauge 412 smooths the needle by displaying the average IPS over the last five seconds, recalculated after every detection of a DICOM image.

In the embodiment shown, the short range history area 420 includes three gauges, a repeat of the current flowrate gauge 412, a virtual gauge 416 showing the average flowrate of images in IPS over the last 5 minutes (in the embodiment shown 1.1 IPS), and a virtual gauge 418 showing the average flowrate over the last hour (1.1 IPS). In the short range history area 420, the period over which the flowrate is averaged is displayed below each gauge. The long range history area 422 also includes three virtual gauges showing averages over longer periods of 4 hours, 24 hours and 1 week as shown by the indicator beneath the gauge. Each of the six gauges is programmable to read from 1 minute to 1 year based on the users right clicking on each gauge and selecting their preferred time setting.

The network card settings area 428 includes information specifically useful to PACS administrators and Modality Service Engineers. The area 428 includes the current IP address of the computing device. In addition, the network card settings area 428 displays the current network interface that the DICOM image traffic monitoring system is monitoring, in this case a Linksys Wireless-G USB Network Adapter. The network card settings area 428 also displays the current connection settings selected by the user for the network interface being monitored and the currently negotiated, or actual, network setting being used by the network interface. This information is useful as often network interfaces will renegotiate connection settings in response to changing conditions on the network. The information displayed in the network card settings area 428 is periodically updated. In an embodiment, the update period is 5 minutes. The network card settings area 428 is also provided with a user selectable button control, titled "verify", that upon selection causes the information in the network card settings area 428 to be updated to the current settings.

A status element 430 is provided to indicate if the DICOM image traffic monitoring system is operating or not. When operating, the status element 430 sequentially displays a series of images (in this case, an sagital MR scan of a healthy human female) as the GUI is redrawn periodically. When paused or not operating, the status element 430 remains unchanged. The status element 430 thus indicates if the monitoring is ongoing.

The image counter element 432 provides an image count from the last reset of the counter or since the DICOM image traffic monitoring system was initialized on the computing device. A user selectable button control element 438 is provided to allow a user to manually reset the image counter to 0.

The display mode element 434 shows the current display mode, which in GUI 400 is "Dicom". The Dicom setting results in the gauges displaying data in IPS. The other mode possible is "Network", which when selected changes the scales on the gauges and the live graph to a raw data flowrate, such as kilobytes per second (KB/S). The raw data flowrate is useful to a PACS administrator or a network support person (information technology or "IT" specialist), while IPS is preferred and best understood by most medical practitioners. This dual reporting/displaying element of this product makes it possibly for non-IT staff and Radiology staff to communicate and co-solve PACS systems problems using similar and mutually understandable units of measurement IPS & kB/S.

The pause element 414, in the form of a familiar stoplight, is a user selectable element that stops the DICOM image traffic monitoring system from redrawing the GUI 400, without interrupting the data monitoring functions of the system. When paused, the virtual red light on top of the element 414 is illuminated. When in normal GUI redraw mode, the virtual green light is illuminated.

In addition, the GUI 400 includes a real time "live graph" element 426. The live graph element 426 is graphical display of the number of images received in a given period. In the embodiment shown, the live graph element 426 includes a vertical axis in IPS and kB/S and a horizontal axis being a timeline with the present moment on the right hand side and most aged on the left hand side. In the GUI 400, the timeline is presented in absolute time with the present moment being about 1:42:30 pm, and displaying approximately the last 30 minutes of image data. In an embodiment, the period displayed by the window is user selectable between the last 30 seconds of data and the last 24 hours worth of data. In addition, a scroll bar is provided allowing the user to scroll back through the graphical timeline data. In an embodiment, the scale of the vertical axis is automatically selected and is based on the largest speed value of the acquired data stream. Alternatively the scale may be user selected.

In an embodiment, a user may position a pointing device over the data in the live graph element 426. In response to the position of the pointing device over the data, a patient name, then total number of images in the burst of data visualized on the graph, the start time of the acquisition, the stop time of the acquisition and the total time of the acquisition corresponding to the data identified by the pointing device may be displayed in a "pop-up" window. This allows a medical practitioner to verify that data for specific patients has been transmitted or received without having to look in a file structure, modality send queue or inspect the actual DICOM Images or transfer logs.

Figure 5:
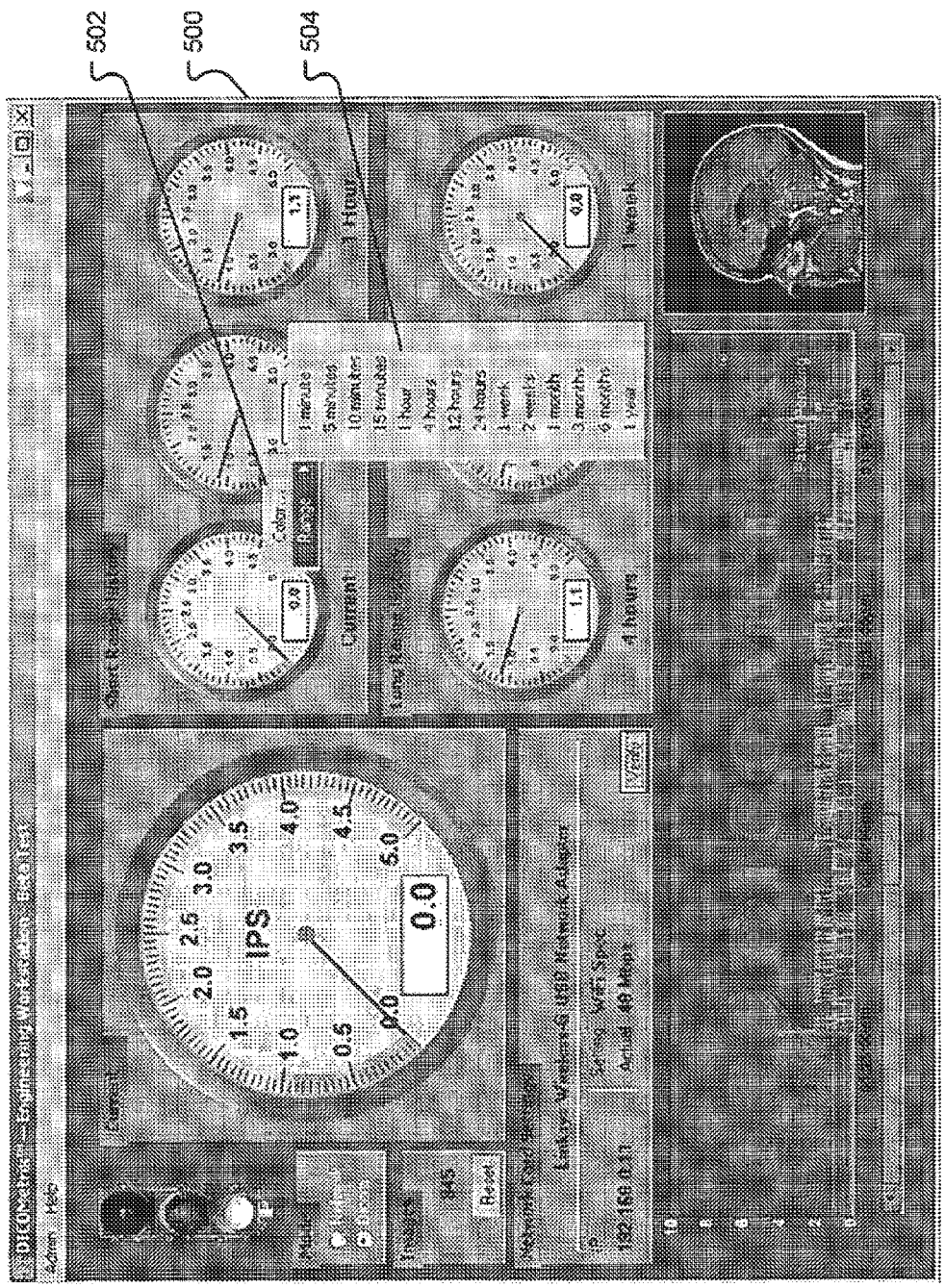
FIG. 5 is an exemplified main display GUI showing a dropdown box for use with an image traffic monitoring system.

FIG. 5 is another exemplified GUI for use with an image traffic monitoring system. The GUI 500 in FIG. 5 displays a dropdown box 502 resulting from a user selection of a virtual gauge, in this case the 5 minute gauge, such as with a right-click using a mouse. The dropdown box includes two selectable elements, one for color which allows the user to change the colors associated with various components of the gauge and another for the range displayed by the gauge. The GUI 500 further shows the user dropdown menu 504 obtained by selecting the range element on the dropdown box 502. The dropdown range menu allows the user to select the range over which the gauge displays the average IPS. In an embodiment, the ranges for each of the gauges in the GUI 500 except the "current" gauge may be changed by a user.

Figure 6:
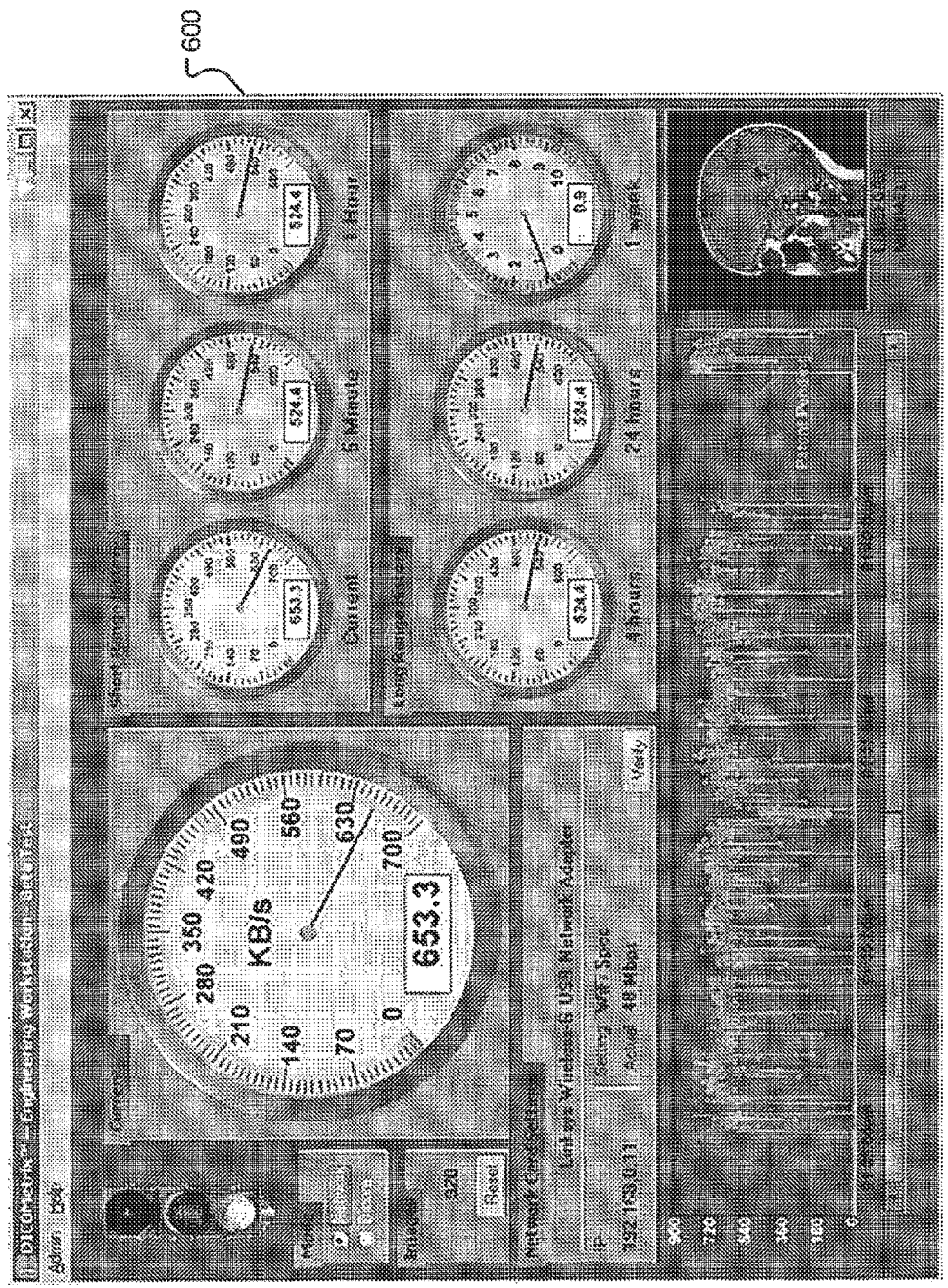
FIG. 6 is yet another exemplified main display GUI for use with an image traffic monitoring system displaying data in units of kilobytes per second.

FIG. 6 is another exemplified main GUI for use with an image traffic monitoring system. The GUI 600 in FIG. 6 corresponds to the GUI 400 shown in FIG. 4 with the exception that the radio selection button for "Network" in the display mode element 434 has been selected. This selection causes all the flowrate displays to change to data quantity flowrate, in this case to KB/s. As mentioned above, in an embodiment of the DICOM image traffic monitoring system data quantity flowrate is always being tracked, even when no DICOM images are being transferred. Thus, the network mode allows a user to verify that the system is working, even when no DICOM images are being transmitted. This display mode is also useful when a computing device's network interface handles digitally encrypted DICOM images.

Figure 7:
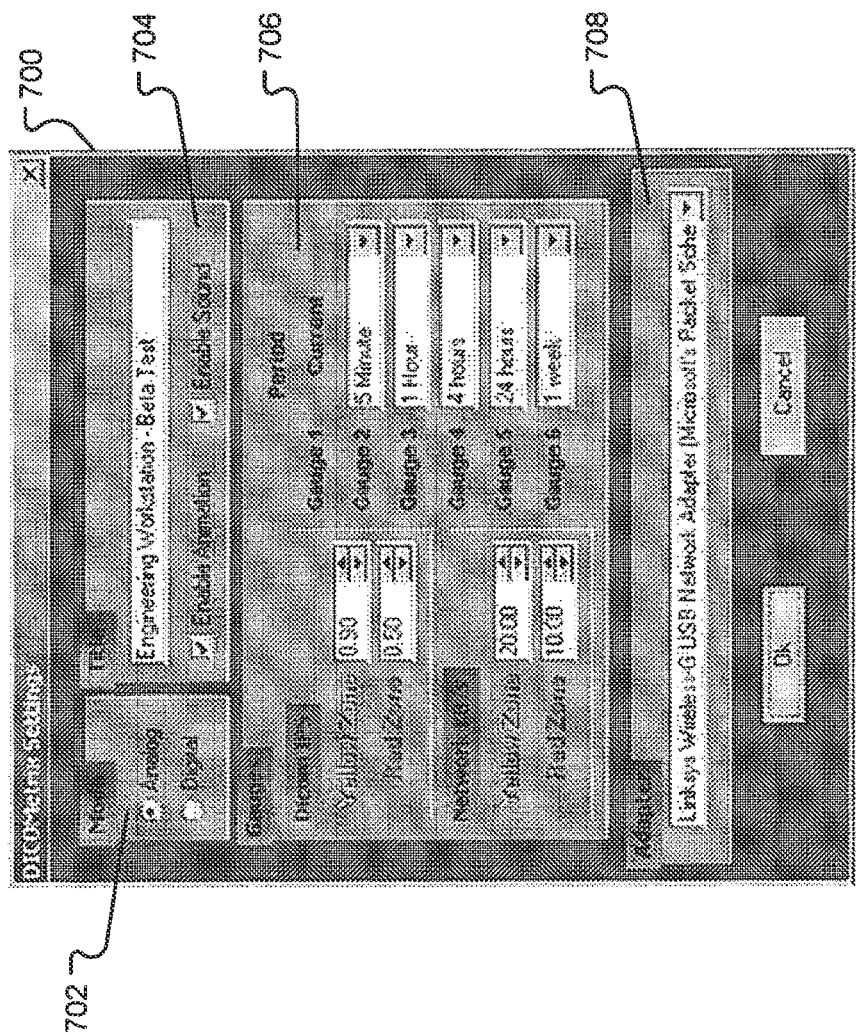
FIG. 7 is an exemplified settings GUI for use with an image traffic monitoring system.

FIG. 7 is another exemplified GUI for use with an image traffic monitoring system. The GUI 700 shown is a settings control GUI 700 that allows a user to change various display setting of the main GUI. In the embodiment shown, settings control GUI 700 includes a display mode area 702, a title area 704, a gauges preferences area 706, and an network interface or adapter selection area 708.

The display mode area 702 includes two radio button controls allowing a user to select between an analog (e.g., with virtual gauges as shown in FIGS. 4-6) main GUI and a digital main GUI (an exemplified digital GUI is presented in FIG. 8, below).

The tile area 704 allows a user to enter a title that appears in a title bar at the top of the main GUI as shown in FIGS. 4-6. In addition, the title area 704 may include a user selectable control from turning on the status element's 430 animation and/or a sound generation module that provides audio feedback to alert the user of certain conditions or provide confirmatory feedback to the user of various user selections specifically the verify button.

The gauges preference area 706 provides another interface through which the user may change the period over which the flowrate data is averaged. In addition, the gauges preference area 706 provides an interface through which the user may select what is displayed as the red zone 408 and the yellow zone 410. The GUI 700 allows a user to independently select different red and yellow zones depending on the display mode, Dicom images or network data KB.

The adapter area 708 allows a user to select from the network interfaces on the computing device. In the embodiment shown, the adapter selection area 708 includes a dropdown box that displays all available network interfaces from which a selection may be made.

The GUI 700 is also provided with an OK button control and a cancel button control for exiting the GUI 700. The OK button control saving all the changes made by the user and the cancel button control making no changes to the previous settings.

Figure 8:
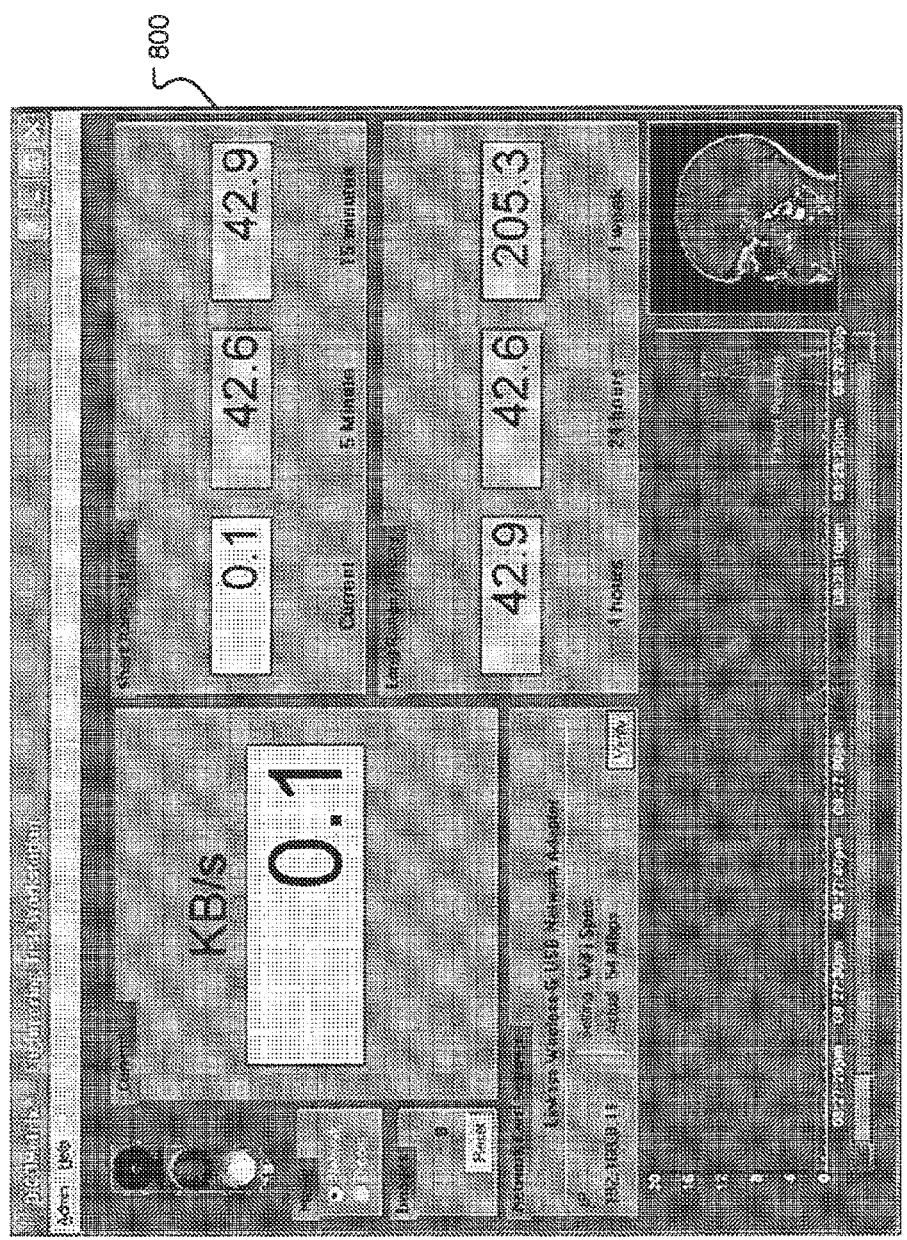
FIG. 8 is another exemplified main GUI displaying data numerically rather than through virtual gauges for use with an image traffic monitoring system.

FIG. 8 is another exemplified GUI for use with an image traffic monitoring system. FIG. 8 illustrates a digital mode display of the main GUI 800. The GUI 800 includes the same areas as described with respect to FIG. 4, however the virtual gauges have been removed leaving only the textual numerical display.

Figure 9:
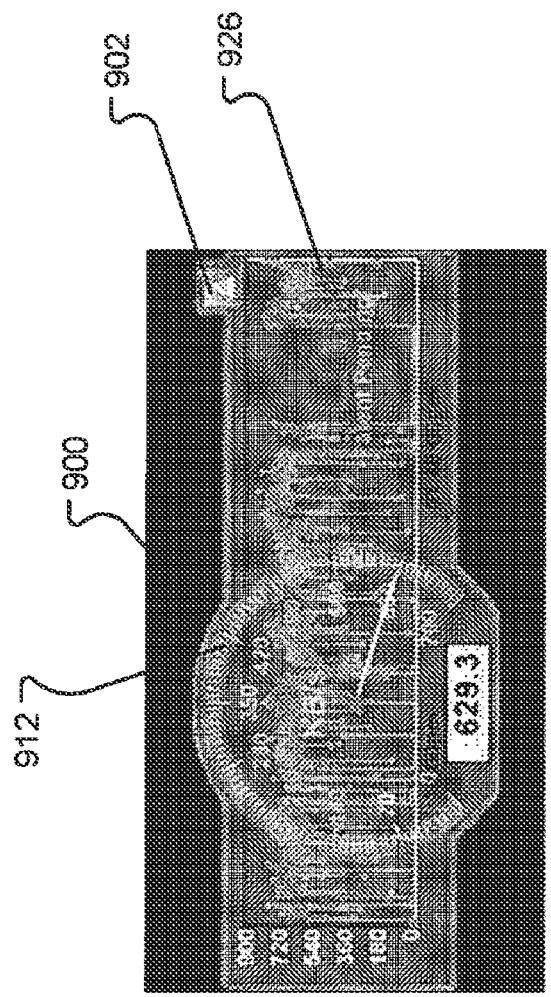
FIG. 9 is an exemplified minimal GUI displaying data in kilobytes per second for use with an image traffic monitoring system.

FIG. 9 is another exemplified GUI for use with an image traffic monitoring system. The GUI 900 illustrated in FIG. 9 is a minimal main GUI 900 showing only a current virtual gauge element 912 overlapping a live graph element 926. In the embodiment shown, the GUI 900 is in network display mode and is displaying flowrate information in KB/s. The current virtual gauge element 912 differs from the corresponding element discussed with respect to FIG. 4 in that it is semitransparent allowing the data in the underlying live graph element 926 to also be simultaneously discerned. The level of transparency is user selectable. The GUI 900 is obtained by selecting a miniature mode from the main GUI 400, such as by selecting the minimize icon in the standard window frame. The minimal GUI 900 is always on top and can be dragged by the user to different locations around the display. The GUI 900 includes a maximize control 902 for returning to the main GUI as shown in FIGS. 4-6.

Figure 10:
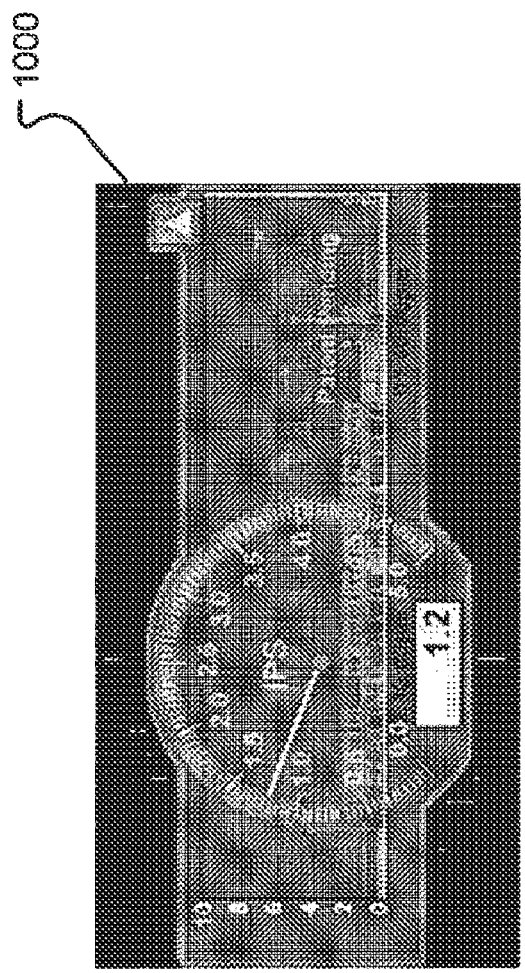
FIG. 10 is another exemplified minimal GUI displaying data in images per second.

FIG. 10 is another exemplified GUI for use with an image traffic monitoring system. The GUI 1000 shown is the same as that of FIG. 9, except that the display mode has been changed to Dicom and thus shows the flowrate data in IPS.

Figure 11A:
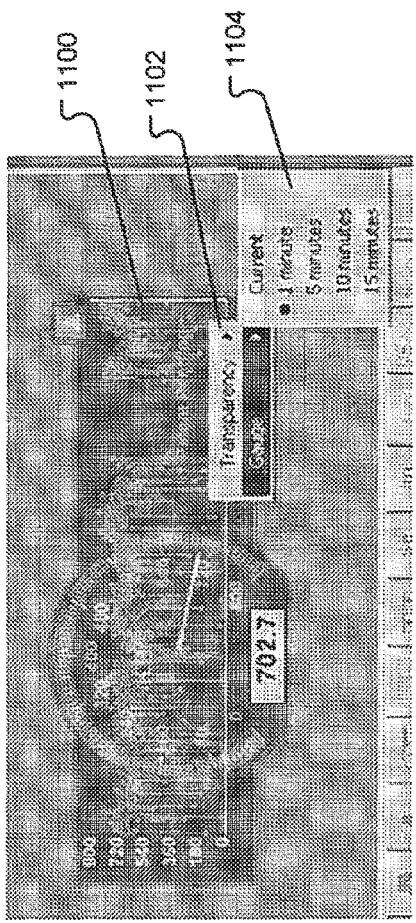
FIGS. 11a and 11b illustrate another exemplified GUI for use with an image traffic monitoring system.
Figure 11B:
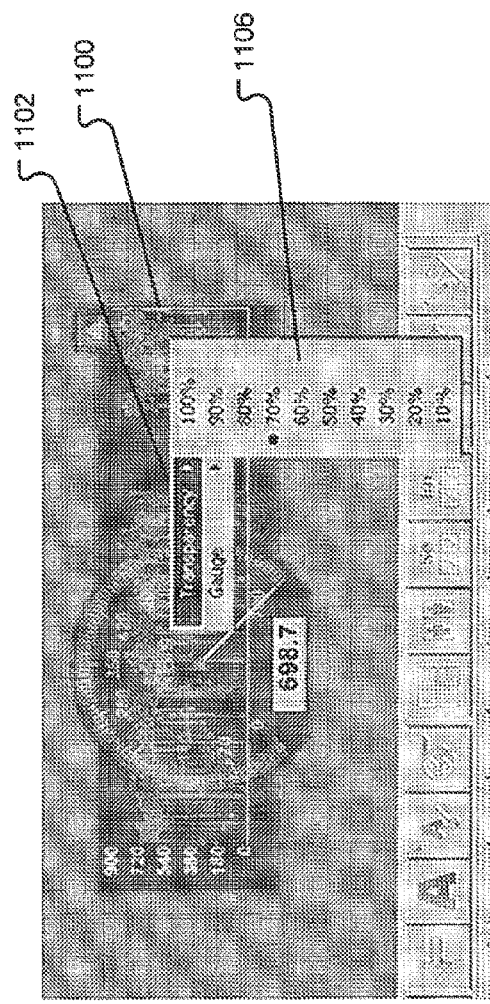

FIGS. 11a and 11b illustrate another exemplified GUI for use with an image traffic monitoring system. FIGS. 11a and 11b illustrate a dropdown box 1102 displayed when a user selects, such as via a right-click on the GUI 1100. Two selectable control elements are shown in the dropdown box 1102, a Transparency control element and a Gauge control element. Selection of the Transparency control element displays a dropdown menu 1106, FIG. 11b, that allows a user to select a transparency setting. Selection of the Gauge control element displays a dropdown menu 1104, FIG. 11a, that allows the user to select different periods for the virtual gauge.

Although not required, the invention is described for convenience in the general context of functional program modules or engines, which may or may not correspond to specific computer-executable instructions that may be executed by a computer, such as a client workstation or a server. Generally, program engines and modules include routines, programs, objects, components, data structures and the like that perform particular tasks or implement particular abstract data types. Although discussed as separate and distinct, one skilled in the art will realize that depending on the implementation choices made during development, some or all of the various engines and modules may combined or further divided into independent sub-modules without changing the overall functionality of the embodiment. In additional, as discussed above in alternative embodiments some or all of the modules described may be distributed throughout other computing devices on the network.

Figure 12:
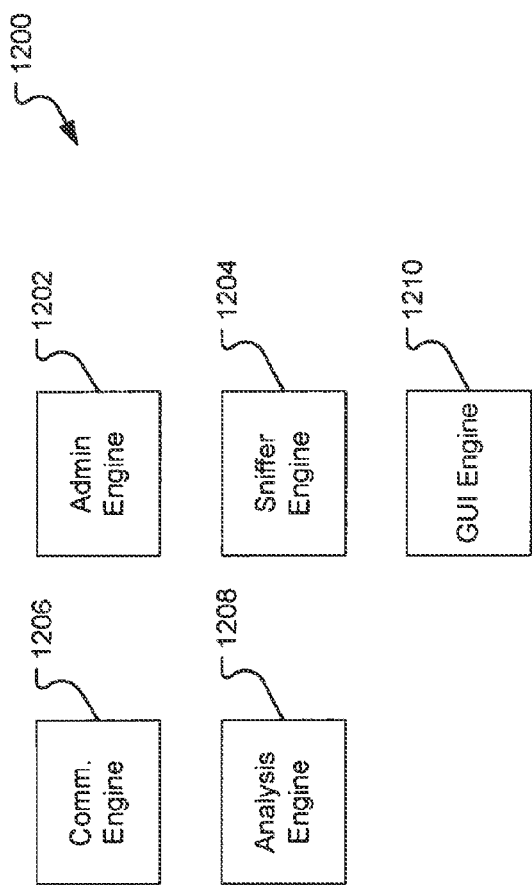
FIG. 12 illustrates a functional block diagram of an embodiment of a DICOM image traffic monitoring system.

FIG. 12 illustrates a functional block diagram of an embodiment of a DICOM image traffic monitoring system. The monitoring system 1200 includes an administrative engine 1202 that senses keyboard and mouse inputs passed through the GUI. These inputs are parsed and stored as necessary. The administration engine 1202 also stores the users parameters in a configuration table and sends out module configuration parameters to all the other software modules to provide the correct data ports examined, assign acquisition trigger IP and temporal thresholds for detecting and stopping data acquisition of the incoming DICOM data packet structure.

The administration engine 1202 passes the acquisition data to the GUI engine 1210 for immediate display. The administration engine 1202 also filters and stores the acquisition data for post processing and sending to a network traffic analysis system, discussed below. None, some or all of the data stored by the DICOM image traffic monitoring system 1200 may be transmitted to the network traffic analysis system, depending on the implementation and the PACS administrator's preferences. In addition, the administration engine 1202 may receive data and commands from the network traffic analysis system, via the communication engine 1206, allowing a PACS administrator to centrally control the operation of the various DICOM image traffic monitoring system 1200s in a PACS network.

The administration engine 1202 monitors and displays the open licensing seats, via the Simple Network Management Protocol (SNMP) engine discussed below, to provide immediate visual status on remaining license seats and to warn when maximum seats have been exceeded and to advise more should be purchased. The administration engine 1202 triggers SNMP alerts to the network traffic analysis system when network sends have stopped for a predetermined amount of time. This provides an alert if the network interface has failed or has become intermittent. Intermittent detection can be sent to the network traffic analysis system for activation of the early warning system.

The administration engine 1202 triggers notification to the network traffic analysis system when the normal baseline DICOM images per second or KB/s values have gone below a pre-assigned remotely programmable threshold. The administration engine 1202 interfaces with DICOM Analysis and Header Display Engine to provide the GUI with the stored DICOM headers for display to PACS administrators.

The DICOM image traffic monitoring system 1200 also includes a sniffer engine 1204. The sniffer engine 1204 handles the acquisition of data from the host computing device's network interface. The sniffer engine 1204 may be customized TCP/IP packet sniffer that reads incoming or outgoing TCP/IP packets at the network interface. The input and display filters sent to this engine come from the administrative engine and are set up from the configuration screens via the GUI. Filters settings may be sent to the sniffer engine 1204 and data read back from the engine's data exchange ports may be stored in arrays for post processing by the administrative engine. The ability may be provided to display the sniffer's raw and pseudo processed data on the GUI. An additional embodiment of the sniffer engine is a virtual adapter that will allow encrypted data streams to be sent from the NIC to the administrative engine for decryption to be able to read the clear text data inside the encrypted data stream. Used in conjunction with a site certificate name, will allow the product to search for the aforementioned Dicom header data and to be able to display IPS data on workstations where the data stream is encrypted/de-crypted for transport over the public Internet to remote PACS workstations at homes and in clinical settings.

The DICOM image traffic monitoring system 1200 shown also includes a communication engine 1206 for interfacing with the network traffic analysis system. The DICOM image traffic monitoring system 1200 shown also includes an analysis engine 1208 for analyzing the data obtained from the sniffer engine 1204 and stored in the image receipt database. The DICOM image traffic system is further provided with a GUI engine 1210 for generating and redrawing the GUIs for the system.

Figure 13:
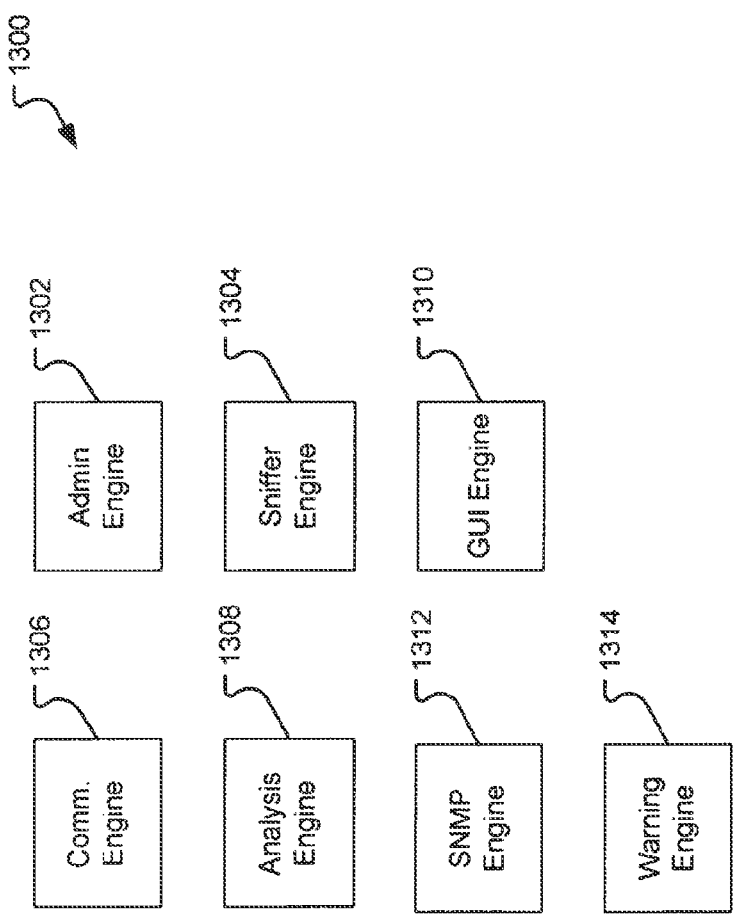
FIG. 13 illustrates a functional block diagram of an embodiment of a DICOM network traffic analysis and early warning system.

FIG. 13 illustrates a functional block diagram of an embodiment of a DICOM network traffic analysis system (referred to as an "Enterprise" system as it evaluates information related to the entire network). The DICOM Enterprise network traffic analysis system 1300 interfaces with the DICOM image traffic monitoring systems on the PACS network in order to analyze the flow of DICOM images on the system. The network traffic analysis system 1300 can receive DICOM image data provided by the monitoring systems, analyze the data and issue alerts or alarms if the analysis identifies a drop in performance on the PACS network.

The Enterprise network traffic analysis system 1300 may be hosted on any computing device in the PACS network.

In an embodiment, the network traffic analysis system 1300 may include all the engines and functionality of a DICOM image traffic monitoring module, Although in an alternative embodiment, the Enterprise network traffic analysis system 1300 is not implemented with the necessary engines to perform monitoring on the host computing device. Thus, an Enterprise network traffic analysis system 1300 may include all of the engines described with reference to FIG. 12 including an administrative engine 1302, a sniffer engine 1304, a GUI engine 1310, a communication engine 1306, and an analysis engine 1308.

In addition, in an embodiment the network traffic analysis system 1300 also includes an SNMP engine 1312. The SNMP engine 1312 provides a control interface between the image traffic monitoring systems and the Enterprise network traffic analysis system. The SNMP engine 1312 monitors the number of monitoring systems 1200 in current operation on the PACS network.

The SNMP engine 1312 further monitors the communications and data from the monitoring systems 1200 for events. Events are conditions stored in an event table that, when detected, cause the Enterprise network traffic analysis system 1300 to perform some function, such as generating an e-mail to a PACS administrator or issuing a message to a pager, through the early warning notification engine 1314. Early Warning System notifies pagers and emails of administrators as to triggered event through triggers of SNMP events at each client equipped workstation or server.

Events that trigger the SNMP Engine to notify administrators are stored in an events table. In an embodiment, exemplified events that can trigger an alert or an alarm include: an IPS of a computing device too low (e.g., below a low-end threshold) or too high (e.g., above a high-end threshold); network interface errors of a computing device, as reported by that device's monitoring system, above a threshold; a lack of response by a computing device to attempts to contact; an excessively high network interface sampling rate at a computing device; receipt of a request for administrator intervention from a monitoring system on a computing device; a dropped connection between the computing device hosting the network traffic analysis system and a computing device; and an invalid license detected for a computing device.

In an embodiment, the Enterprise network traffic analysis system 1300 stores and displays real-time and historical DICOM image statistics, and headers, from each computing device equipped with a monitoring system 1200. The data from the monitoring systems 1200 may be stored into variable file formats for post display processing, thus allowing a PACS administrator to run reports and perform trending analyses.

In an embodiment, the Enterprise network traffic analysis system 1300 is capable of retrieving any of the information displayed or stored by a DICOM image traffic monitoring system 1200. In addition, through the SNMP engine, a administrator may request that such information be updated, such as by remotely commanding the image traffic monitoring system 1200 to determine the current settings of the network interface.

Figure 14:
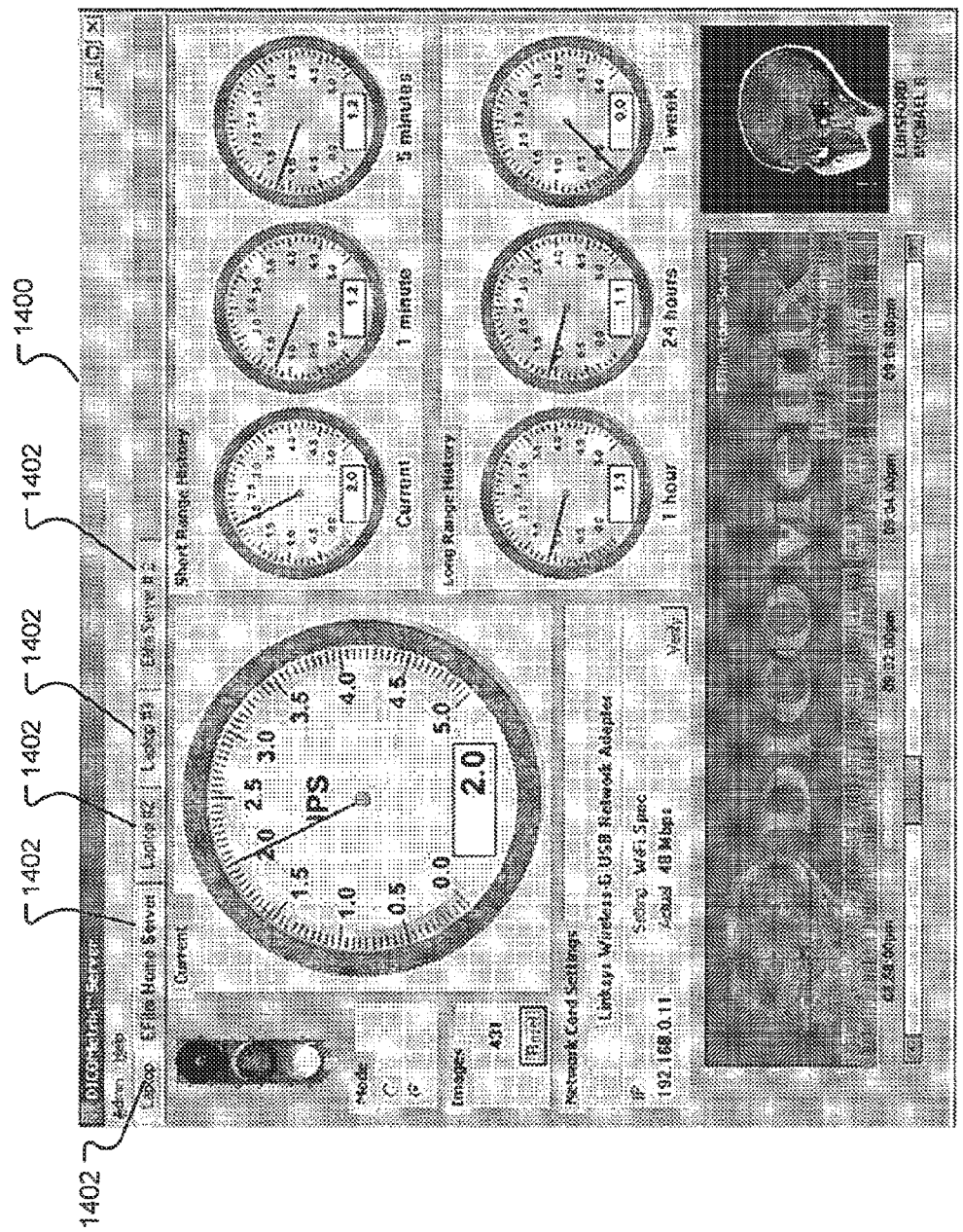
FIG. 14 is an exemplified main Enterprise GUI for use with an Enterprise network traffic analysis system.

FIG. 14 is an exemplified main GUI 1400 for use with an Enterprise network traffic analysis system 1300. The Enterprise GUI 1400 includes many of the same elements and areas shown in FIGS. 4 and 6. In addition, the Enterprise GUI 1400 includes a set of tabbed pages 1402. Each tabbed page 1402 corresponds to a different modality being monitored by the Enterprise network traffic analysis system 1300. User selection of a tab 1402 causes the associated page GUI to be displayed to the user. In the embodiment shown, the tab 1402 titled EFilm Home Server is selected and the GUI 1400 for that modality is displayed showing the current information received from DICOM image traffic monitoring system on the EFilm Home Server modality. Thus, the Enterprise GUI 1400 can provide the network administrator with the same information discussed with reference to FIGS. 4 and 6 for each modality on the network.

It will be clear that the present invention is well adapted to attain the ends and advantages mentioned as well as those inherent therein. While a presently preferred embodiment has been described for purposes of this disclosure, various changes and modifications may be made which are well within the scope of the present invention. For example, in an alternative embodiment, rather than recording each header and then performing a calculation using the recorded information, a periodic sampling of image headers may be performed. At or close to a scheudled time for redraw of the GUI, the monitoring system may attempt to detect an image header as described above. Upon detection of an image header, the type of modality is determined. Next a lookup table or some other accessible reference is used to identify a representative image size in KB or some other data measurement for the modality. The representatvie image size is then compared with the current data flowrate through the network interface to obtain an average image flowrate. For example, the current flowrate in KB/s may be divided by the representative size in KB per image to obtain a rough measure of images per second. Numerous other changes may be made which will readily suggest themselves to those skilled in the art and which are encompassed in the spirit of the invention disclosed and as defined in the appended claims.

What is claimed is:

1. A system for monitoring performance of a medical data network without violating patient confidentiality comprising:
a first image traffic monitoring system operating on a first computing device, the first image traffic monitoring system detecting the transfer of confidential images between the first computing device and the medical data network and storing non-confidential image traffic data, including non-confidential data copied from the confidential images and data describing the number of confidential images transferred over time;
a network traffic analysis system operating on a second computing device, the network traffic analysis system receiving image traffic data from the first image traffic monitoring system and generating warnings to an administrator of the medical data network if the image traffic data indicates that the transfer of confidential images between the first computing device and the medical data network falls below a threshold set by the administrator.

2. The system of claim 1 wherein the network traffic analysis system further comprises:

a graphical user interface (GUI) engine adapted to generate GUIs on the second computing device, the GUIs displaying the number of confidential images transferred over time between the first computing device and the medical data network.

3. The system of claim 1 wherein the first image traffic monitoring system detects non-confidential headers of the confidential images and transmits at least one copy of a non-confidential header to the network traffic analysis system and wherein the graphical user interface (GUI) engine is adapted to display the at least one copy of the non-confidential header.

4. The system of claim 1 wherein the first image traffic monitoring system is adapted to detect current network interface settings of the first computing device and transmit the settings to the Enterprise network traffic analysis system.

5. The system of claim 1 wherein the image traffic data is transmitted to the Enterprise network traffic analysis system substantially immediately upon detection of the transfer of a confidential image and the network traffic analysis system is further adapted to display substantially immediately upon receipt of the image traffic data at least a portion of the image traffic data.

6. The system of claim 1 wherein the image traffic data includes at least one patient name associated with a confidential image and the network traffic analysis system is further adapted to display the patient name when displaying the image traffic data describing the number of confidential images transferred over time.

* * * * *